United States Patent
Heidlas et al.

(10) Patent No.: US 6,288,130 B1
(45) Date of Patent: Sep. 11, 2001

(54) OIL-FREE GLYCEROPHOSPHOLIPID FORMULATIONS AND METHOD FOR THE PRODUCTION THEREOF

(75) Inventors: Jürgen Heidlas; Karl-Heinz Zirzow, both of Trostberg; Johann Wiesmüller, Garching; Martin Ober, Altenmarkt; Franz Michlbauer, Kirchweidach; Jürgen Graefe, Trostberg, all of (DE)

(73) Assignee: SKW Trostberg Aktiengesellschaft, Trostberg (DE)

( * ) Notice: Subject to any disclaimer, the term of this patent is extended or adjusted under 35 U.S.C. 154(b) by 0 days.

(21) Appl. No.: 09/381,527

(22) PCT Filed: Mar. 26, 1998

(86) PCT No.: PCT/EP98/01796

§ 371 Date: Sep. 20, 1999

§ 102(e) Date: Sep. 20, 1999

(87) PCT Pub. No.: WO98/43492

PCT Pub. Date: Oct. 8, 1998

(30) Foreign Application Priority Data

Mar. 27, 1997 (DE) .............................. 197 13 096

(51) Int. Cl.$^7$ .............................. B01F 17/14; C07F 9/02; A23J 7/00
(52) U.S. Cl. .............................. 516/56; 554/83; 426/662
(58) Field of Search .............................. 516/56; 426/662, 426/602, 478; 554/83

(56) References Cited

U.S. PATENT DOCUMENTS

| | | | |
|---|---|---|---|
| 4,452,743 | * 6/1984 | Gunther | 554/83 |
| 4,681,617 | 7/1987 | Ghyczy et al. | 504/206 |
| 5,597,602 | * 1/1997 | Peter et al. | 426/478 |
| 5,711,965 | 1/1998 | Ghyczy et al. | 424/450 |
| 5,741,513 | 4/1998 | Ghyczy et al. | 424/450 |

FOREIGN PATENT DOCUMENTS

| | | |
|---|---|---|
| 231233 | 2/1911 | (DE) . |
| 4440831 | 5/1996 | (DE) . |
| 9319617 | 10/1993 | (WO) . |
| 9401004 | 1/1994 | (WO) . |
| 9421763 | 9/1994 | (WO) . |

OTHER PUBLICATIONS

Chemical Abstracts, vol. 84, No. 15, Apr. 12, 1976, abstract No. 104092g, p. 455; col. 2, XP002074168 & JP 75 030 595 A (Nisshin Oil Mills, Ltd) Oct. 2, 1975.
Patent Abstracts of Japan, vol. 097, o. 003, Mar. 31, 1997 & JP 08 301885 A (Kyowa Hakko Kogyo Co Ltd; Iwase Cosfa KK); Nov. 19, 1996.
Patent Abstracts of Japan, vol. 006, No. 049 (C–096), Mar. 31, 1982 & JP 56 163746A (Tsuji Seiyu KK), Dec. 16, 1981.
Database WPI, Section CH, Week 8417, Derwent Publications Ltd., London GB; Class D23, AN 84–104888 XP002074169 & JP 59 048 492 A (Asahi Denka Kogyo KK).
Database WPI, Section Ch, Week 8325, Derwent Publicaitios Ltd., London, GB; Class D13, AN 83–59625K XP002074170 & JP 58 078 545 (Asahi Denka Kogio KK).
Chem. Abst 96 (6), 40734f, 1982–Month Unknown, Japanese Appln. No. 79147956.

* cited by examiner

Primary Examiner—Daniel S. Metzmaier

(57) ABSTRACT

The invention relates to oil-free glycerophospholipid formulations which contain a homogeneous mixture of glycerophospholipids and an anhydrous, liquid polyol compound such as glycerol in a molar ratio of 1:0.1 to 1. These formulations are produced, eg, by extracting a starting material consisting of an oil-containing glycerophospholipid (mixture) and the polyol component with a compressed hydrocarbon (mixture) in a rectifying column. The oil-free formulation can be obtained from the melt at the bottom of the column in the form of free-flowing powder, which is ideally suited for stabilising oil-in-water emulsions.

10 Claims, No Drawings

OIL-FREE GLYCEROPHOSPHOLIPID FORMULATIONS AND METHOD FOR THE PRODUCTION THEREOF

FIELD OF THE INVENTION

This invention relates to oil-free glycerophospholipid formulations and a method of producing them.

BACKGROUND AND SUMMARY OF THE INVENTION

As a rule, commercially available natural lecithins are mixtures of various glycerophospholipids, for example phosphatidyl choline, phosphatidyl ethanolamine, phosphatidyl inositol, phosphatidyl serine and phosphatidic acid, of vegetable, animal or microbial origin, in which the proportions of the individual glycerophospholipids and of polar minor constituents can vary over a wide range. There are various methods available with which the proportions of certain glycerophospholipids in the natural mixtures can be increased, or with which the glycerophospholipids can be isolated in pure form.

Vegetable lecithins are usually by-products of the industrial production of vegetable oils from, for example, soybean, sunflower or rape seed. During the traditional refining process, so-called "degumming", the lecithins are obtained, together with vegetable oils (triglycerides), as so-called "raw lecithin", with an oil content between 50 and 70%. After a filtration step and standardisation to a certain lecithin content ("acetone insoluble"), these oil-containing raw lecithins can be used as emulsifiers, eg, in the production of food and of cosmetic and technical products.

For certain applications, however, oil-free lecithins are required, which dissolve better in water due to their oil-containing counterparts. The HLB value (as a measure of the solubility of an emulsifier in water, scale 1 [=insoluble in water] to 20 [=soluble in water]) of commercially available oil-free lecithins is about 7. However, the limited wettability of the deoiled lecithins in cold water poses a technical constraint.

Various methods have been described with which oil-free lecithins can be produced, also on an industrial scale. These include, in particular, solvent extraction with acetone or ethanol, and the more recent method of gas extraction with nearly-critical propane. From the point of view of potential solvent residues and the formation of by-products, extraction with compressed propane ranks as particularly advantageous, since, on the one hand, the processing conditions are mild on the product, and, on the other hand, propane is completely inert under the customary processing conditions. An added advantage consists in that the possible formation of undesired by-products can be entirely precluded. The disadvantage of this method, however, is that the water-wettability of lecithins deoiled with compressed propane is markedly inferior to that of corresponding acetone-deoiled qualities, and this puts distinct limitations on the practical applications.

The physiological importance of glycerophospholipids, and especially of phosphatidyl choline, as a component of biological membranes has been known for a long time. In the wake of numerous scientific studies in which lecithin was proved to have various beneficial effects in the human body, lecithins have been developed over the past few years which are intended especially as dietary supplements or as so-called nutraceuticals for a health-conscious consumer segment. In many cases lecithin fractions are used which have been enriched with certain glycerophospholipids, eg, fractions containing an elevated phosphatidyl choline content, which can be prepared, eg, by means of solvent extraction with ethanol. These products are usually offered in the form of powders, granules or tablets. In the production of lecithin-containing beverages, however, the limited solubility or dispersibility of the glycerophospholipids in water often constitutes a limitation, which is why, from a technical point of view, the production of oil-free lecithins with improved solubility or dispersibility in water is desirable. In the pharmaceuticals industry, due to traditionally good experience, use is made predominantly of lecithins obtained from eggs, and sometimes also of soya-based lecithins enriched with phosphatidyl choline. Besides peroral dosage forms, these lecithins are available in forms for intravenous administration, eg, as parenteral fat emulsions. On account of the high natural phosphatidyl choline content, fat-free egg-based lecithins are particularly suitable for drug formulations in reverse micelles (so-called liposomes). The range of applications of lecithins used pharmaceutically could also be enlarged if their solubility or dispersibility in water were improved.

Various methods are known for improving the solubility or dispersibility of lecithin in water. As was already mentioned, the water-solubility of natural lecithins is generally improved if they are freed as completely as possible of their oil content. In addition, chemical or enzymatic modifications have been suggested, eg, acetylation of the free amino groups by treating the lecithin with acetic anhydride, hydroxylation of the C=C double bonds of the unsaturated fatty acid radicals contained in lecithin, eg, with peracetic acid or hydrogen peroxide, acetylation of the amino groups with subsequent hydroxylation of C=C double bonds, and chemical or enzymatic partial hydrolysis, during which a fatty acid is split off from the phospholipid, to form so-called lyso-lecithins. Whereas—not least on account of legal stipulations—the first three of these modification processes have only been implemented in technical applications, the partially hydrolysed lyso-lecithins, by virtue of their being physiologically safe and of their resulting legislative acceptance, have enjoyed wide distribution during the past few years in food and in pharmaceutical active-ingredient formulations.

A decisive improvement in the water-dispersibility of lyso-lecithins can be achieved if they are likewise freed as completely as possible of their oil content. However, the production of these deoiled lyso-lecithins is extremely tedious, since besides the partial hydrolysis, there is the additional deoiling step, resulting in high costs for the overall process and consequently also for the product.

Native lecithins also differ in their physiological efficacy from chemically or enzymatically modified lecithins. In cases where lecithins are used pharmaceutically or as dietary supplements also on account of their natural physiological properties, products produced by way of modification processes are usually not suitable.

To improve the water-dispersibility of lecithins, a great variety of lecithin formulations have been proposed, eg, with ethanol/water (JP 81,163,745), with ethanol/propylene glycol/glycerol (JP 81,163,746), with ethanol/water/propylene glycol/glycerol (JP 81,163,747) and with sugar esters/propylene glycol (JP 75,30,595). What all of these formulations have in common is that relatively large amounts of additives are required in order to obtain a suitable pasty consistency for the further incorporation of the emulsifier formulations. This has the disadvantage that the surface-active lecithin, the actual emulsifying active ingredient in the formulation, is heavily diluted, and relatively large amounts of surface-active formulation aids are introduced into the mixture.

In view of these disadvantages of the prior art, the object of this invention was thus to provide oil-free glycerophospholipid formulations which show enhanced solubility and/or dispersibility in water, as well as a suitable method of producing them, while avoiding the shortcomings and limitations of already-known products and their production methods.

This object was established with oil-free formulations which contain a homogeneous mixture of (a) one or more glycerophospholipids and (b) one or more anhydrous, liquid polyol compounds with at least two hydroxyl groups, the components (a) and (b) being present in a molar ratio of 1:0.1 to 1. The average molecular weights of the glycerophospholipids can be used as the calculation basis for this molar ratio.

Surprisingly, it was found that the solubility and dispersibility of oil-free lecithins in water can be improved significantly by mixing them homogeneously with polyol compounds in the proportions cited. The formulations of the invention are, for one, extremely stable in water and do not dissociate into their individual components, and, for the other, they dissolve distinctly better in water than do the corresponding oil-free lecithins currently on the market.

DETAILED DESCRIPTION OF THE INVENTION

In terms of the invention, "oil-free" means that the formulation contains a maximum of 3 wt. %, preferably a maximum of 2 wt. % and more preferably a maximum of 1 wt. % of oil components, ie, triglycerides, expressed in terms of the total weight of glycerophospholipid and polyol.

The term "anhydrous" as used in the invention means that the polyols used to prepare the formulation contain a maximum of 5 wt. %, preferably a maximum of 3 wt. % of water, expressed in terms of the weight of polyol.

Glycerophospholipids are, in terms of the invention, preferably naturally occurring glycerophospholipids, ie, glycerols esterified with 2 fatty acid radicals and one phosphate radical. The term also covers chemically and/or enzymatically modified glycerophospholipids, especially lysolecithins, and mixtures of natural and modified glycerophospholipids.

Polyol compounds are, in terms of this invention, preferably liquid polyols with 2 to 6 carbon atoms, with special preference being given to diols and/or triols such as ethylene glycol, propylene glycol, glycerol or mixtures thereof. Glycerol, in particular, which on account of its physiological nature can be used safely in food, dietary supplements and pharmaceutical products, is especially interesting because of its legislative acceptance. In principle, however, liquid polyol compounds with higher molecular weights can also be used.

According to the invention, the polyol compound is only used in the formulation in the concentration necessary to achieve the desired water dispersibility. The maximum proportion of polyol compound in a formulation with good water dispersibility is that which corresponds to a molar ratio of 1:1. It is thus possible to prepare powdery lecithin products which have good flow properties and which dissolve well in water, because up to a molar ratio of approximately 0.4, the proportion of polyol does not influence the consistency of the non-formulated, deoiled lecithins. A molar ratio of polyol component to glycerophospholipid of 0.1 to 0.6:1 has proved to be especially suitable. Together with the high proportion of surface-active glycerophospholipid, the excellent product consistency of the formulations of the invention represent a considerable improvement on the water-soluble lecithin formulations which have been commercially available until now. Compared to the chemically or enzymatically modified glycerophospholipids, the preferred formulations containing unmodified glycerophospholipids are distinguished by their unchanged natural properties.

To obtain the outstanding properties of the formulations, it is essential to prepare a homogeneous and stable oil-free mixture of the glycerophospholipid component and the anhydrous polyol component. Since oil-free glycerophospholipids as such are sometimes subject to decomposition on melting, and a homogeneous formulation is not by all means obtained with small quantities of the liquid polyol compound, it is generally expedient to add suitable solvents during the preparation of the formulations of the invention, and to remove them again subsequently.

Besides the glycerophospholipid component and the polyol component, the formulations of the invention can contain up to 5 wt. % of minor constituents, especially natural minor constituents such as carbohydrates, eg, monosaccharides, or carbohydrate derivatives.

A two-step method has proved particularly suitable for producing the formulations of the invention. In step (a) one or more oil-containing glycerophospholipids is mixed homogeneously with one or more anhydrous, liquid polyol compounds in a molar ratio of glycerophospholipid to polyol of 1:0.01 to 1, preferably at temperatures between 20 and 80° C. and maybe with the addition of max. 300 wt. %—expressed in terms of the polyol component—of a $C_{1-4}$ alcohol. As starting materials, preference is given to the so-called standardised oil-containing lecithins ("raw lecithin"), which are commercially available. Since, in certain cases, an increase in viscosity is to be observed during homogeneous mixing of the oil-containing glycerophospholipids with the polyol compound, especially where the proportion of polyol compound is higher, the method of the invention provides for the addition in such cases of a short-chain alcohol. Methanol, ethanol, n- or isopropanol or arbitrary mixtures thereof are especially suitable here.

The homogeneous mixture obtained after vigorous stirring is then subjected to a suitable extraction process in step (b). During this process, the oil which in this case can be seen as a technical aid—and the alcohol—if any was used—contained in the glycerophospholipid are largely removed. To this end, it is preferable to extract the mixture obtained according to (a) with an extracting agent containing propane and/or butane. It is especially beneficial to conduct the extraction in a rectifying column at a pressure between 10 and 100 bar and at temperatures from 30 to 100° C., the mixture being separated into a liquid phase containing oil and maybe $C_{1-4}$ alcohol, and a melt containing glycerophospholipid and polyol. The liquid phase is discharged as top product and the melt as bottom product. The oil-free glycerophospholipid formulation is obtained from the melt.

The extraction process of step (b) is conducted in a column, preferably as a continuous, countercurrent process. It has proved especially beneficial for the desired reduction in oil content if propane with an addition of up to 25% butane is used as extracting agent. For special applications, however, the invention also provides for use of an extracting agent consisting of propane and up to 90 wt. % dimethyl ether (DME).

For improved separation of the mixture into two phases (upper phase/lower phase), one variant of the method provides for a temperature gradient in the column, the gradient being adjusted such that the temperature at the top of the column is 5 to 50° C. higher than that at the bottom.

To free the bottom product from extracting agent, the melt can be discharged from the column into an ambient-pressure environment; largely due to the reduction in pressure, most of the gaseous extracting agent (mixture) is removed spontaneously. The bottom product is subsequently freed completely of any remaining extracting agent by reducing the pressure further, for example by means of a vacuum pump, and/or by raising the temperature.

To free the top product, ie, the fraction containing oil and maybe alcohol, of extracting agent, evaporation by means of pressure reduction and/or temperature increase is recommended. Extracting agent removed in this way can then be recompressed and/or condensed, and can, if desired, be used again in the extraction process.

On account of their excellent solubility and dispersibility in water, the glycerophospholipid formulations obtained with the method of the invention are preferably suited for stabilising oil-in-water emulsions, for example, of typical creams.

When performed on a model system with phosphatidyl choline and glycerol, probability-density calculations to determine binding energies led to a surprising result, namely that the associates produced according to the method of the invention can have a binding stability, which is stabilised by hydrogen ridges, of up to 300 kJ/mol. These high binding energies, which correspond in magnitude to a single covalent bond, explain the high stability of the formulations according to the invention, and the fact that even in aqueous systems, they do not dissociate spontaneously into their individual components.

The following examples serve to illustrate a typical method of producing the claimed formulations.

DETAILED DESCRIPTION OF PREFERRED EMBODIMENTS

EXAMPLE 1

A raw soybean lecithin with an acetone-soluble content ("oil content") of 35 wt. % and an acetone-insoluble content ("lecithin content") of 65 wt. % is stirred intensively with 2 wt. % anhydrous glycerol at 45 to 50° C. The homogenous mixture is supplied by means of a high-pressure pump to an extraction column, approximately in the middle. The rectifying section of the column has about 5 and the stripping section about 7 theoretical stages. Compressed propane under a pressure of 60 bar serves as extracting agent. At the feed stage of the column the temperature is about 75° C., at the top of the column 85° C. and at the bottom of the column 65° C. The ratio of the mixture supplied (feed) to the extracting agent propane is on average 5 wt. % (±1 wt. %). The empty-pipe speed of the extracting agent in the column is 2 mm/s The extracting agent conveyed out of the column head, loaded with oil but free of glycerol, is evaporated in a separator at approximately 70° C. and 8 bar, and thus freed of oil. The oil-free formulation formed according to the method of the invention (oil content<2 wt. %) is discharged at the bottom of the column into an ambient-pressure environment by way of an arrangement of nozzles. Due to spontaneous evaporation of the propane, the formulation cools and a free-flowing powder is obtained. The proportion of glycerol in the formulation is 3 wt. %; this corresponds to a molar ratio of 0.2 (calculated on the basis of an average molecular weight of 700 daltons for the glycerophospholipids). The formulated product shows excellent dispersibility in water.

EXAMPLE 2

A raw soybean lecithin with an acetone-soluble content ("oil content") of 35 wt. % and an acetone-insoluble content ("lecithin content") of 65 wt. % is stirred intensively with 3.5 wt. % anhydrous glycerol and, to reduce the viscosity, with 3 wt. % ethanol (99.8%) at 45 to 50° C. The homogenous mixture is supplied by means of a high-pressure pump to an extraction column, approximately in the middle. The rectifying section of the column has about 5 and the stripping section about 7 theoretical stages. Compressed propane under a pressure of 50 bar serves as extracting agent. At the feed stage of the column the temperature is about 70° C., at the top of the column 80° C. and at the bottom of the column 60° C. The ratio of the mixture supplied (feed) to the extracting agent propane is on average 7 wt. % (±1 wt. %). The empty-pipe speed of the extracting agent in the column is 2 mm/s.

The extracting agent conveyed out of the column head, loaded with oil and ethanol but free of glycerol, is evaporated in a separator at approximately 65° C. and 8 bar, and thus freed of the oil and almost all of the ethanol.. The oil-free formulation formed according to the method of the invention (oil content <2 wt. %) is discharged at the bottom of the column into an ambient-pressure environment by way of an arrangement of nozzles. Due to spontaneous evaporation of the propane, the formulation cools and a free-flowing powder is obtained. The proportion of glycerol in the formulation is 5 wt. %; this corresponds to a molar ratio of 0.35 (calculated on the basis of an average molecular weight of 700 daltons for the glycerophospholipids). The formulated product shows excellent dispersibility in water.

EXAMPLE 3

A raw soybean lecithin with an acetone-soluble content ("oil content") of 35 wt. % and an acetone-insoluble content ("lecithin content") of 65 wt. % is stirred intensively with 6.5 wt. % anhydrous glycerol and, to reduce the viscosity, with 8 wt. % ethanol (99.8%) at 45 to 50° C. The homogenous mixture is supplied by means of a high-pressure pump to an extraction column, approximately in the middle. The rectifying section of the column has about 5 and the stripping section about 7 theoretical stages. A compressed mixture of propane and about 10 wt. % butane under a pressure of 65 bar serves as extracting agent. At the feed stage of the column the temperature is about 75° C., at the top of the column 85° C. and at the bottom of the column 65° C. The ratio of the mixture supplied (feed) to the extracting agent propane is on average 10 wt. % (±1 wt. %). The empty-pipe speed of the extracting agent in the column is 2 mm/s.

The extracting agent conveyed out of the column head, loaded with oil and ethanol but free of glycerol, is evaporated in a separator at approximately 60° C. and 7 bar, and thus freed of the oil and almost all of the ethanol. The oil-free formulation formed according to the method of the invention (oil content <3 wt. %) is discharged at the bottom of the column into an ambient-pressure environment by way of an arrangement of nozzles. Due to spontaneous evaporation of the propane/butane mixture, the formulation cools and an initially free-flowing powder is obtained. After about an hour, however, the powder collapses and tends to stick. The proportion of glycerol in the formulation is 10 wt. %; this corresponds to a molar ratio of 0.7 (calculated on the basis of an average molecular weight of 700 daltons for the glycerophospholipids). The formulated product shows excellent dispersibility in water.

What is claimed is:

1. A method of producing the oil-free glycerophospholipid formulation comprising:
   (a) homogeneously mixing one or more oil-containing glycerophospholipids with one or more anhydrous, liquid polyol compounds in a molar ratio of glycerophospholipid to polyol compound of 1:0.01 to 1, and optionally C1–C4 mono-alcohol, and
   (b) subjecting the mixture obtained in step (a) to an extraction process during which the any oil and C1–C4 mono-alcohol is removed; and
      wherein in step (b), the mixture is extracted with an extracting agent containing at least one of the group consisting of propane and butane at a pressure between 10 and 100 bar and temperatures from 30 to 100° C. in a rectifying column having a top and bottom, and separating the mixture into a liquid phase containing oil, and a melt containing the glycerophospholipid, polyol and optionally 0 to 3 wt % oil by weight of the final formulation; and discharging the liquid phase as top product and the melt as bottom product, the oil-free glycerophospholipid formulation being obtained from the melt.

2. The method of claim 1, wherein step (a) further comprises the addition of max. 300 wt. % expressed in terms of the polyol component of a C1–C4 mono-alcohol and in step (b) the monoalcohol added in step (a) is removed.

3. The method of claim 2, wherein said alcohol at least one C1–C4 mono-alcohol selected from the group consisting methanol, ethanol, n-propanol and isopropanol.

4. The method of claim 1, wherein propane with a proportion of up to 25 wt. % butane is used in step (b) as extracting agent.

5. The method of claim 1, wherein propane with a proportion of up to 90 wt. % dimethyl ether is used in step (b) as extracting agent.

6. The method according of claim 1, wherein the extraction is conducted as a continuous, countercurrent process.

7. The method of claim 1, wherein a temperature gradient is adjusted in the rectifying column such that the temperature at the top of the column is 5 to 50° C. higher than that at the bottom.

8. The method of claim 1, wherein the extracting agent is removed from the product at the bottom of the rectifying column by one of reducing the pressure or raising the temperature.

9. The method of claim 1, wherein the extracting agent is removed from the product at the top of the rectifying column in a separator by one of reducing the pressure or raising the temperature.

10. The method of claim 1, wherein the extracting agent is removed and subsequently recompressed or condensed and recycled.

* * * * *